United States Patent [19]

Lesieur et al.

[11] Patent Number: 5,703,121

[45] Date of Patent: Dec. 30, 1997

[54] METHOD OF TREATING DISORDERS OF THE MELATONINERGIC SYSTEM AND A CERTAIN BENZOFURAN CONTAINING COMPOUND

[75] Inventors: Daniel Lesieur, Gondecourt; Eric Fourmaintraux, St Martin/Boulogne S/Mer; Patrick Depreux, Armentieres; Philippe Delagrange, Issy Les Moulineaux; Pierre Renard, Versailles; Béatrice Guardiola-Lemaitre, Saind Cloud, all of France

[73] Assignee: Adir Et Compagnie, Courbevoie, France

[21] Appl. No.: 584,466

[22] Filed: Jan. 11, 1996

[30] Foreign Application Priority Data

Jan. 11, 1995 [FR] France .................... 95 00238

[51] Int. Cl.$^6$ .................... A61K 31/34; C07D 307/81
[52] U.S. Cl. .................... 514/469; 549/467
[58] Field of Search .................... 549/467; 514/469

[56] References Cited

U.S. PATENT DOCUMENTS 3,226,402 12/1965 Schoetensack et al. ............ 549/467
3,407,210 10/1968 Schoetensack et al. ............ 549/467
5,308,866 5/1994 Lesieur et al. .................... 514/469

OTHER PUBLICATIONS

Tobler et al., Journal of Pineal Research 16, 1994, pp. 26–32.

*Primary Examiner*—Bernard Dentz
*Attorney, Agent, or Firm*—The Firm of Gordon W. Hueschen

[57] ABSTRACT

The invention relates to a compound selected from those of formula (I):

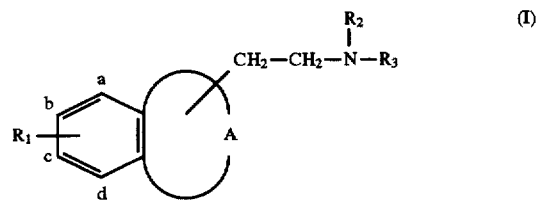

in which: $R_1$, $R_2$, $R_3$ and A are as defined in the description, and Medicinal product containing the same useful for treating a disorder of the melatoninergic system.

9 Claims, No Drawings

METHOD OF TREATING DISORDERS OF THE MELATONINERGIC SYSTEM AND A CERTAIN BENZOFURAN CONTAINING COMPOUND

The invention relates to novel alkylated (hetero)cyclic compounds, to a process for their preparation and to the pharmaceutical compositions which contain them.

The invention describes novel alkylated (hetero)cyclic compounds which prove to be powerful ligands for melatoninergic receptors.

In the last ten years, many studies have demonstrated the fundamental role of melatonin (5-methoxy-N-acetyltryptamine) in controlling circadian rhythm and endocrine functions, and the melatonin receptors have been characterized and localized.

Besides their beneficial action on disorders of circadian rhythm (J. Neurosurg., 1985, 63, pp 321–341) and on sleeping disorders (Psychopharmacology, 1990, 100, pp 222–226), ligands for the melatoninergic system possess advantageous pharmacological properties with regard to the central nervous system, in particular anxiolytic and antipsychotic properties (Neuropharmacology of Pineal Secretions, 1990, 8 (3–4), pp 264–272) and analgesic properties (Pharmacopsychiat., 1987, 20, pp 222–223) as well as for the treatment of Parkinson's disease (J. Neurosurg., 1985, 63, pp 321–341) and Alzheimer's disease (Brain Research, 1990, 528, pp 170–174). Similarly, these compounds have shown an activity on certain cancers (Melatonin-clinical Perspectives, Oxford University Press, 1988, page 164–165), on ovulation (Science 1987, 227, pp 714–720), and on diabetes (Clinical endocrinology, 1986, 24, pp 359–364).

Compounds whch make it possible to act on the melatoninergic system are thus excellent medicinal products, for clinicians, for the treatment of the pathologies mentioned above.

The invention relates to the compounds of formula (I):

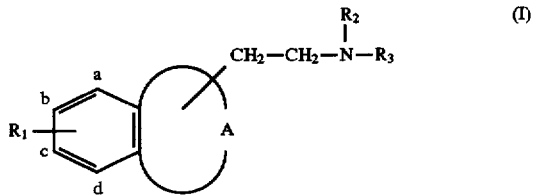

in which:

R$_1$ represents a radical chosen from alkyl, substituted alkyl, cycloalkyl, substituted cycloalkyl, cycloalkylalkyl and substituted cycloalkylalkyl, A forms, with the benzene ring to which it is attached, a cyclic group chosen from benzofuran and 2,3-dihydrobenzofuran, R$_2$ represents a hydrogen or an alkyl, R$_3$ represents:

a group R$_{31}$:

with X representing a sulfur or an oxygen and R$_4$ representing a hydrogen or a radical R$_{41}$ chosen from alkyl, substituted alkyl, alkenyl, alkynyl, cycloalkyl, substituted cycloalkyl, cycloalkylalkyl and substituted cycloalkylalkyl, or a group of formula (R$_{32}$):

with X' representing a sulfur or an oxygen and R$_5$ representing a hydrogen or a radical chosen from alkyl, substituted alkyl, cycloalkyl, substituted cycloalkyl, cycloalkylalkyl and substituted cycloalkylalkyl, it being understood that in the description of formula (I), and except where otherwise mentioned:

the terms "alkyl" and "alkoxy" denote linear or branched groups containing from 1 to 6 carbon atoms, the terms "alkenyl" and "alkynyl" denote linear or branched groups containing from 2 to 6 atoms, the term "cycloalkyl" denotes a group of 3 to 8 carbon atoms, the term "substituted" associated with the alkyl radical means that this radical is substituted with one or more substituents chosen from halogen, alkyl, hydroxyl and alkoxy, the term "substituted" associated with the "cycloalkyl" and "cycloalkylalkyl" radicals means that this radical is substituted with one or more radicals or groups chosen from halogen, alkyl and oxo, and the enantiomers and diastereoisomers thereof.

The invention relates more particularly to the compounds of formula (I) in which, taken separately or together, R$_1$ represents an alkyl, R$_1$ represents a (C$_2$–C$_6$)alkyl, R$_1$ represents an ethyl, R$_1$ represents a propyl, R$_1$ represents a butyl, A forms, with the benzene ring to which it is attached, a benzofuran, A forms, with the benzene ring to which it is attached, a 2,3-dihydrobenzofuran, R$_2$ represents a hydrogen, R$_2$ represents an alkyl, R$_3$ represents a group R$_{31}$ as defined in formula (I), R$_3$ represents a group R$_{32}$ as defined in formula (I), R$_4$ represents a hydrogen atom, R$_4$ represents an alkyl, R$_4$ represents a cycloalkyl, R$_4$ represents an alkenyl, R$_5$ represents a hydrogen, R$_5$ represents an alkyl, R$_5$ represents a cycloalkyl, X represents an oxygen, X represents a sulfur, X' represents an oxygen, or X' represents a sulfur.

For example, the invention relates to the specific compounds of formula (I) corresponding to the respective formulae (1) and (2):

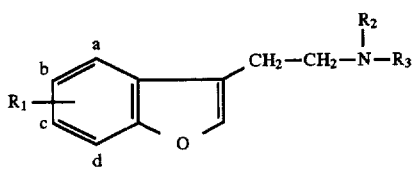

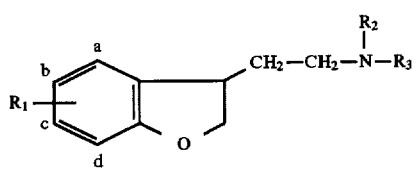

The invention relates particularly to the compounds of formula (I), for example the specific compounds of formulae (1) and (2), as defined above in which $R_1$ is:

in position a of the benzene ring, in position b of the benzene ring, in position c of the benzene ring, or in position d of the benzene ring.

For example, the invention relates to the compounds of formula (I) in which $R_1$ is in position b of the benzo ring.

The invention specifically relates to the following compounds:

N-[2-(5-ethylbenzofuran-3-yl)ethyl]acetamide,

N-[2-(5-ethylbenzofuran-3-yl)ethyl]cyclobutanecarboxamide.

The alkyl radicals present in formula (I) may specifically be chosen from methyl, ethyl, n-propyl, isopropyl, n-butyl, isobutyl, sec-butyl, tert-butyl, pentyl and hexyl, The alkoxy radicals present in formula (I) may be chosen from methoxy, ethoxy, n-propoxy, isopropoxy, n-butoxy, isobutoxy, sec-butoxy, tert-butoxy, pentyloxy and hexyloxy.

The halogens present in formula (I) may be chosen from bromine, chlorine, fluorine and iodine.

The cycloalkyls present in formula (I) may be chosen from cyclopropyl, cyclobutyl, cyclopentyl, cyclohexyl, cycloheptyl and cyclooctyl.

The invention also relates to the process for the preparation of the compounds of formula (I), wherein:

a compound of formula (II):

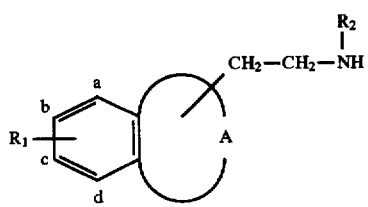

in which $R_1$, $R_2$ and A are as defined in formula (I), is reacted either with formic acid or with a compound of formula (IIIa) or (IIIb):

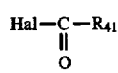 (IIIa)

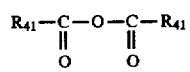 (IIIb)

in which $R_{41}$ is as defined in formula (I) and Hal represents a halogen, in order to obtain the compounds of formula (I/a):

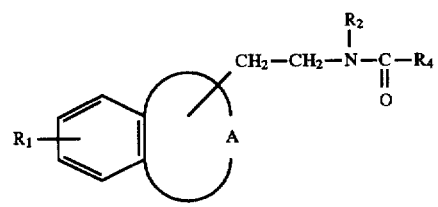

in which $R_1$, $R_2$, $R_4$ and A are as defined above, which compounds of formula (I/a) are treated with Lawesson's reagent in order to obtain the compounds of formula (I/a'):

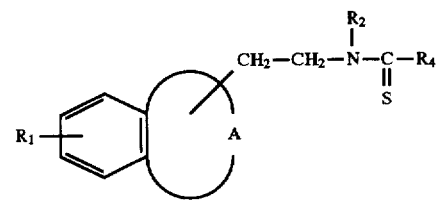

in which $R_1$, $R_2$, $R_4$ and A are as defined above, or with a compound of formula (IV):

$$X'=C=N-R_5 \qquad (IV)$$

in which X' and $R_5$ are as defined in formula (I) in order to obtain the compounds of formula (I/b):

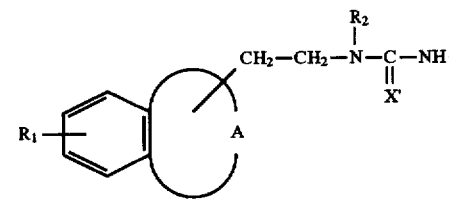

in which $R_1$, $R_2$, $R_5$, A and X' are as defined above, the compounds of formulae (I/a), (I/a') and (I/b) forming the set of compounds of formula (I), which compounds of formula (I) are, where appropriate, separated into the various enantiomers or diastereoisomers thereof.

For example, the invention covers the process for the preparation of the compounds of formula (I/c):

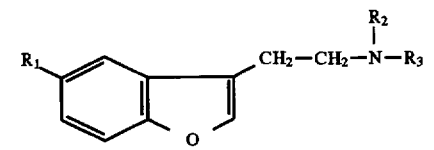

in which $R_1$, $R_2$ and $R_3$ are as defined in formula (I), wherein:

a compound of formula (II/b):

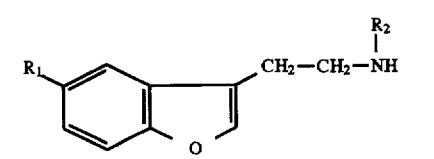

in which $R_1$ and $R_2$ are defined as above, is reacted either with formic acid or with a compound of formula (IIIa) or (IIIb) as defined above, in order to obtain the compounds of formula (I/d):

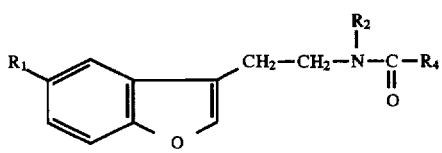

in which $R_1$, $R_2$ and $R_4$ are as defined above, which compounds are then treated with Lawesson's reagent in order to obtain the compounds of formula (I/d'):

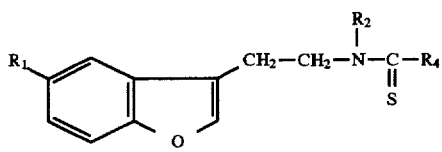

in which $R_1$, $R_2$ and $R_4$ are as defined above, or with a compound of formula (IV) as defined above, in order to obtain the compounds of formula (I/e):

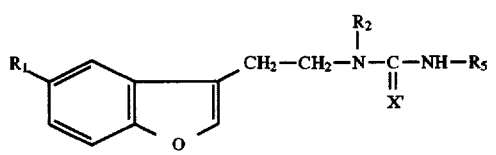

in which $R_1$, $R_2$, $R_5$ and X' are as defined above, the compounds of formula (I/d), (I/d') and (I/e) forming the set of compounds of formula (I/c), it being possible for the compounds of formula (I/c) to be separated into the various enantiomers or diastereoisomers thereof.

The starting materials used in the processes described above are either commercial or are readily accessible to those skilled in the art by means of the literature and the preparation examples given below.

For example, it is possible to prepare the compounds of formula (II/a):

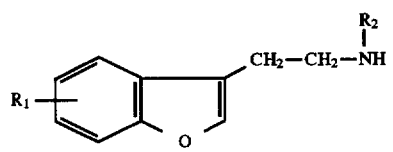

in which $R_1$ and $R_2$ are as defined in formula (I), by reaction of a compound of formula (V):

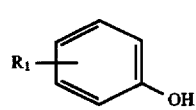

in which $R_1$ is as defined above, with acetic anhydride in order to obtain a compound of formula (VI):

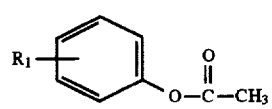

in which $R_1$ is as defined above, which compound of formula (VI) is reacted with a Lewis acid in order to obtain a compound of formula (VII):

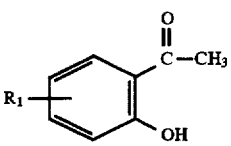

in which $R_1$ is as defined above, which compound of formula (VII) is reacted with cupric bromide in order to obtain the compound of formula (VIII):

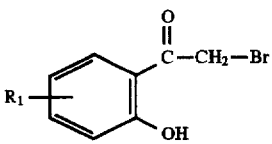

in which $R_1$ is as defined above, which compound of formula (VIII) is cyclized in order to obtain a compound of formula (IX):

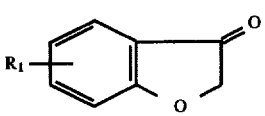

in which $R_1$ is as defined in formula (I), which compound of formula (IX) is then reacted with diethyl cyanomethyl phosphonate in the presence of sodium hydride in order to obtain a compound of formula (X):

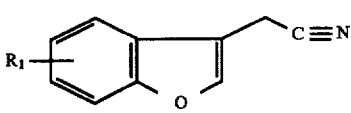

which is then hydrogenated and optionally alkylated on the nitrogen in order to obtain a compound of formula (II/a):

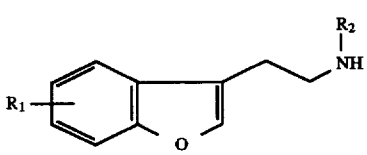

in which $R_1$ is as defined above, and it being possible for the compounds of formula (II/a) to be salified with a pharmaceutically acceptable acid.

For example, it is possible to prepare the compounds of formula (II/b):

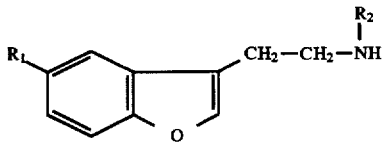

in which $R_1$ and $R_2$ are as defined in formula (I), by reaction of a compound of formula (V/b):

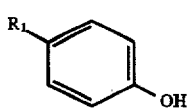

in which $R_1$ is as defined above, with acetic anhydride in order to obtain a compound of formula (VI/b):

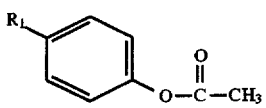
(VI/b)

in which $R_1$ is as defined above, which compound of formula (VI/b) is reacted with a Lewis acid in order to obtain a compound of formula (VII/b):

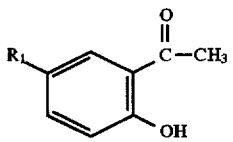
(VII/b)

in which $R_1$ is as defined above, which compound of formula (VII/b) is reacted with cupric bromide in order to obtain the compound of formula (VIII/b):

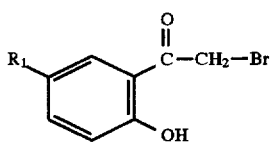
(VIII/b)

in which $R_1$ is as defined above,
which compound of formula (VIII/b) is cyclized in order to obtain a compound of formula (IX/b):

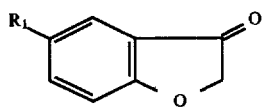
(IX/b)

in which $R_1$ is as defined in formula (I), which compound of formula (IX/b) is then reacted with diethyl cyanomethyl phosphonate in the presence of sodium hydride in order to obtain a compound of formula (X/b):

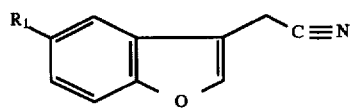
(X/b)

which is then hydrogenated and optionally alkylated on the nitrogen in order to obtain a compound of formula (II/b):

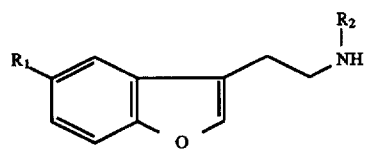
(II/b)

in which $R_1$ is as defined above, and it being possible for the compounds of formula (II/b) to be salified with a pharmaceutically acceptable acid.

Among the pharmaceutically acceptable acids which may be used to form an addition salt with the compounds of formula (II), there may be mentioned, by way of non-limiting examples, hydrochloric acid, sulfuric acid, phosphoric acid, tartaric acid, malic acid, maleic acid, fumaric acid, oxalic acid, methanesulfonic acid, ethanesulfonic acid, camphoric acid and citric acid.

The 2,3-dihydrobenzofuran derivatives required for the preparation of the compounds of formula (I), in which A forms, with the benzo ring to which it is attached, a 2,3-dihydrobenzofuran, are readily accessible to those skilled in the art by controlled reduction of the corresponding benzofuran derivative.

The invention also covers the process for the preparation of a compound of formula (I/f):

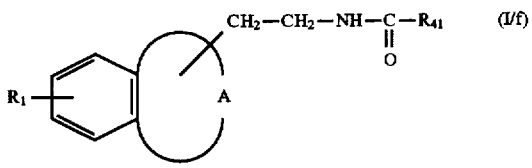
(I/f)

in which A, $R_1$ and $R_{41}$ are as defined in formula (I), by reaction, in the presence of Raney nickel and hydrogen, of a derivative of formula (XI):

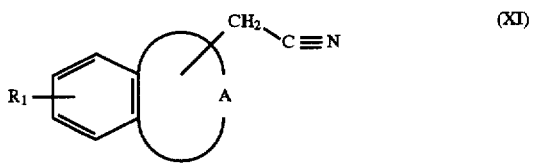
(XI)

in which $R_1$ is as defined above, with a compound of formula (III/a) or (III/b):

(III/a)

(III/b)

in which $R_{41}$ is as defined above and Hal represents a halogen.

For example, the invention also covers the process for the preparation of a compound of formula (I/f'):

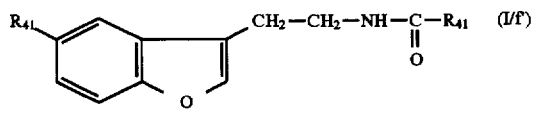
(I/f')

in which A, $R_1$ and $R_{41}$ are as defined in formula (I), by reaction, in the presence of Raney nickel and hydrogen, of a derivative of formula (XI'):

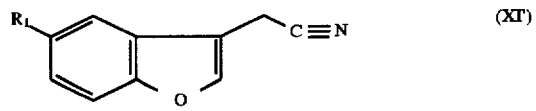
(XI')

in which $R_1$ is as defined above, with a compound of formula (III/a) or (III/b):

(III/a)

(III/b)

in which $R_{41}$ is as defined above and Hal represents a halogen.

The compounds of formula (I) possess pharmacological properties which are very advantageous for clinicians.

The compounds of the invention and the pharmaceutical compositions containing them prove to be useful for the treatment of disorders of the melatoninergic system.

Pharmacological study of the derivatives of the invention has indeed shown that they were not toxic, were endowed with a very selective affinity for the melatonin receptors and had considerable activities on the central nervous system and, in particular, therapeutic properties with regard to sleeping disorders, anxiolytic, antipsychotic and analgesic properties were found, as well as therapeutic properties with regard to microcirculation, which make it possible to establish that the products of the invention are useful in the treatment of stress, sleeping disorders, anxiety, seasonal depressions, cardiovascular pathologies, insomnia and fatigue due to changes in time zone, schizophrenia, panic attacks, melancholia, appetite disorders, obesity, insomnia, psychotic disorders, epilepsy, Parkinson's disease, senile dementia, various disorders associated with normal or pathological ageing, migraine, memory loss, Alzheimer's disease, and disorders of cerebral circulation. In another field of activity, it is seen that the products of the invention possess immunomodulatory and ovulation-inhibitory properties and that they can be used in anticancer treatment.

The compounds will preferably be used in the treatment of seasonal depressions, sleeping disorders, cardiovascular pathologies, insomnia and fatigue due to changes in time zone, appetite disorders and obesity.

For example, the compounds will be used in the treatment of seasonal depressions and sleeping disorders.

Another subject of the present invention is the pharmaceutical compositions containing the products of formula (I) in combination with one or more pharmaceutically acceptable excipients.

Among the pharmaceutical compositions according to the invention which may be mentioned more particularly are those which are suitable for oral, parenteral, nasal per- or transcutaneous, rectal, perlingual, ocular or respiratory administration, and in particular simple or coated tablets, sublingual tablets, sachets, packets, gelatin capsules, glossettes, lozenges, suppositories, creams, salves, dermal gels, and drinkable or injectable ampules.

The dosage varies depending on the sex, age and weight of the patient, the route of administration, the nature of the therapeutic indication, or on treatments which may be associated, and is graded between 0.1 mg and 1 g per 24 hours taken in 1 or 2 doses, more particularly between 1 and 100 mg, for example between 1 and 10 mg.

The examples which follow illustrate the invention, but do not limit it in any way.

PREPARATION 1

(5-Ethylbenzofuran-3-yl)acetonitrile

Stage A: 4-Ethylphenyl acetate

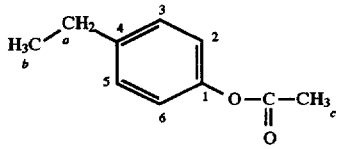

Reactants:

4-ethylphenol: 20 g Acetic anhydride: 100 ml
Procedure:

The acetic anhydride is mixed with the 4-ethylphenol in a 250 ml ground-necked conical flask. The mixture is left stirring for 5 hours.

The mixture is allowed to return to room temperature and is then poured into 1 liter of water and crushed ice. This mixture is extracted three times with ether. The ether phases are washed several times with 10% $K_2CO_3$ solution to neutral pH. The ether phase is dried over $CaCl_2$ and driven to dryness on a rotor vapor: a yellowish oil is obtained.

Characteristics:

MW: 164.20 g.mol$^{-1}$ Appearance: yellowish oil Yield: 84%
Infrared spectroscopic analysis:

2840 to 3000 cm$^{-1}$: νCH 1760 cm$^{-1}$: νC=O
Proton NMR spectroscopic analysis (80 MHz, CDCl$_3$):

δ=1.15 ppm (triplet, 3H): Hb δ=2.25 ppm (quartet, 2H): Ha δ=2.65 ppm (singlet, 3H): Hc δ=6.8 to 7.5 ppm (multiplet, 4H): aromatic H Stage B: 5-Ethyl-2-hydroxyacetophenone

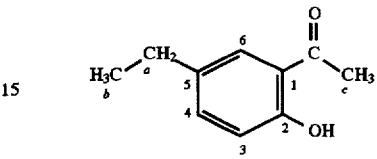

Reactants:

4-ethylphenyl acetate: 19.36 g aluminum trichloride: 38.8 g
Procedure:

The ester is stirred in a 100 ml round-bottomed flask and AlCl$_3$ is introduced portionwise.

The flask is placed in an oil bath preheated to 100° C., and is left stirring for 1 h 30.

The hot reaction medium is poured onto 1 kg of crushed ice. It is extracted three times with ether and the organic phases are then washed with water to neutral pH. The ether phase is dried over CaCl$_2$ and the solvent is evaporated off: a yellow oil is obtained.

Characteristics:

MW: 164.20 g.mol$^{-1}$ Appearance: yellow oil Yield: 89%
Infrared Spectroscopic Analysis:

2840–3000 cm$^{-1}$: νCH 1635 cm$^{-1}$: νC=O
Proton NMR Spectroscopic Analysis (80 MHz, CDCl$_3$):

δ=1.20 ppm (triplet, 3H): H$_b$ δ=2.60 ppm (quartet, 2H): H$_a$ δ=2.60 ppm (singlet, 3H): H$_c$ δ=6.90 ppm (doublet, 1H): H$_3$ Jo=8.40 Hz δ=7.30 ppm (doublet, 1H): H$_6$ Jm=2.1 Hz δ=7.55 ppm (doubled doublet, 1H): H$_4$ Jo=8.40 Hz; Jm=2,1 Hz δ=12,10 ppm (singlet, 1H): OH Stage C: 5-Ethyl-2-hydroxybromoacetophenone:

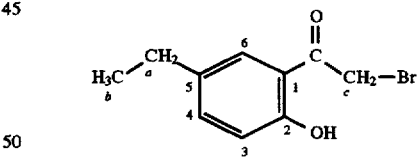

Reactants:

5-ethyl-2-hydroxyacetophenone: 18 g cupric bromide (CuBr$_2$): 52.85 g ethyl acetate/CHCl$_3$ (1/1)
Procedure:

The cupric bromide and the 5-ethyl-2-hydroxyacetophenone in the ethyl acetate/CHCl$_3$ (90-90) mixture are mixed together in a 250 ml ground-necked conical flask. The medium is maintained at reflux for 15 hours. The inorganic precipitate is filtered off and rinsed with ethyl acetate. The filtrate is driven to dryness. The residue is taken up in ethyl acetate and rinsed several times with water. The organic phase is dried over MgSO$_4$ and the solvent is evaporated off. The residue obtained is then purified by chromatography on a column of silica gel eluted with a CHCl$_2$/cyclohexane/toluene mixture (4/4/2).

Characteristics:

MW: 243.11 g. mol⁻¹ Appearance: yellow oil Yield: 56%
Infrared Spectroscopic Analysis:
2840–3000 cm⁻¹: νCH 1630 cm⁻¹: νC=O
Proton NMR Spectroscopic Analysis (80 MHz, CDCl₃):
δ=1.25 ppm (triplet, 3H): $H_b$ δ=2.60 ppm (quartet, 2H): $H_a$ δ=4.45 ppm (singlet, 2H): $H_c$ δ=6.9 ppm (doublet, 1H): $H_3$ δ=7.4 ppm (doublet, 1H): $H_6$ δ=7.5ppm (doubled doublet, 1H): $H_4$ δ=11.6 ppm (singlet, 1H): OH (exchangeable in D₂O)

|  | Microanalysis: | | |
|---|---|---|---|
|  | % C | % H | % Br |
| % theory | 49.41 | 4.56 | 32.87 |
| % found | 49.08 | 4.34 | 33.19 |

Stage D: 5-Ethylbenzofuranone:

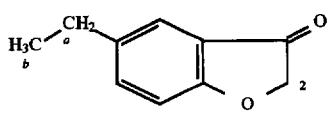

Reactants:
5-ethyl-2-hydroxybromoacetophenone: 5 g K₂CO₃: 3.13 g Acetone: 50 ml
Procedure:

The 5-ethyl-2-hydroxybromoacetophenone is mixed in the acetone in a 100 ml round-bottomed flask. The K₂CO₃ is added and the mixture is left stirring for 4 hours at room temperature.

The inorganic material is drained off and rinsed with acetone, and the filtrate is driven to dryness. The residue is then purified by chromatography on a column of silica eluted with a cyclohexane/ethyl acetate mixture (9/1).
Characteristics:

MW: 162.19 g.mol⁻¹ Appearance: orange-colored oil Yield: 60%
Infrared Spectroscopic Analysis:
2840–3000 cm⁻¹: νCH 1700 cm⁻¹: νC=O
Proton NMR Spectroscopic Analysis (300 MHz, CDCl₃):

δ=1.24 ppm (triplet, 3H): $H_b$ δ=2.66 ppm (quartet, 2H): $H_a$ δ=4.62 ppm (singlet, 2H): $H_2$ δ=7.06 ppm (doublet, 1H): $H_7$ δ=7.46 ppm (multiplet, 2H): $H_6$+$H_4$ Stage E: (5-Ethylbenzofuran-3-yl)acetonitrile:

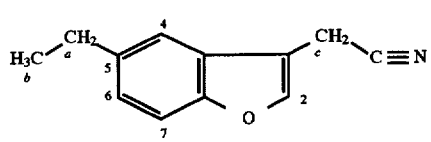

Reactants:
5-ethylbenzofuranone: 2 g diethyl cyanomethyl phosphonate: 3.28 g sodium hydride (60%) (NaH): 0.74 g tetrahydrofuran (THF): 25 ml
Procedure:

15 ml of anhydrous THF are stirred under N₂ in a 100 ml two-necked round-bottomed flask. NaH is added portionwise, followed by dropwise addition of the diethyl cyanomethyl phosphonate using a dropping funnel. The mixture is left stirring for 1 hour at room temperature and under nitrogen. The 5-ethylbenzofuranone predissolved in 10 ml of THF is then added via the dropping funnel. The mixture is left stirring for 1 hour. The medium is poured into 250 ml of water and extracted three times with ether. The ether phases are washed with water until the washing waters are colorless. The ether phase is dried over CaCl₂ and the solvent is evaporated off.

The oily residue obtained is then purified by chromatography on a column of silica eluted with a cyclohexane/ethyl acetate mixture (9/1).
Characteristics:

MW: 185.23 g.mol⁻¹ Appearance: yellow oil Yield: 49%
Infrared Spectroscopic Analysis:
2840–3000 cm⁻¹: νCH 2240 cm⁻¹: νC≡N
Proton NMR Spectroscopic Analysis (80 MHz, CDCl₃):

δ=1.26 ppm (triplet, 3H): $H_b$ δ=2.77 ppm (quartet, 2H): $H_a$ δ=3.72 ppm (singlet, 2H): $H_2$ δ=7 to 7.75 ppm (multiplet, 3H): aromatic H

|  | Microanalysis: | | |
|---|---|---|---|
|  | % C | % H | % N |
| theory | 77.81 | 5.99 | 7.56 |
| found | 77.53 | 6.18 | 7.15 |

PREPARATIONS 2 TO 6

Working as in preparation 1, but using the appropriately substituted phenol in Stage A, the following preparations are obtained:
Preparation 2: (5-propylbenzofuran-3-yl)acetonitrile
Preparation 3: (5-butylbenzofuran-3-yl)acetonitrile
Preparation 4: (5-hexylbenzofuran-3-yl)acetonitrile
Preparation 5: (5-cyclopropylbenzofuran-3-yl)acetonitrile
Preparation 6: (5-cyclopropylmethylbenzofuran-3-yl) acetonitrile

PREPARATIONS 7 TO 9

The following preparations are obtained by subjecting the amines derived from preparations 1 to 3 to a controlled reduction.
Preparation 7: N-[2-(5-ethyl-2,3-dihydrobenzofuran-3-yl) ethyl]amine
Preparation 8: N-[2-(5-propyl-2,3-dihydrobenzofuran-3-yl) ethyl]amine
Preparation 9: N-[2-(5-butyl-2,3-dihydrobenzofuran-3-yl) ethyl]amine
Preparation 10: (6-ethylbenzofuran-3-yl)acetonitrile

EXAMPLE 1

N-[2-(5-ethylbenzofuran-3-yl)ethyl]acetamide

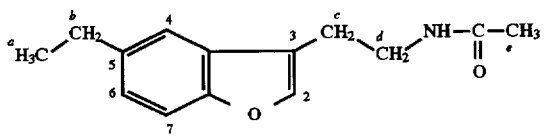

Reactants:
(5-ethylbenzofuran-3-yl)acetonitrile (preparation 1): 4.45 g Acetic acid: 90 ml Raney nickel (50%): 1.5 g H₂: 60 bar
Procedure:

The compound of preparation 1 predissolved in the acetic anhydride, and the Raney nickel are introduced into a 125 ml autoclave. The system is placed under an hydrogen pressure of 60 bar and is left stirring at 50° C. for 5 hours. The nickel is filtered off and rinsed with 95° ethanol and the filtrate is driven to dryness. The residue is taken up in 150 ml of water and basified with 10% NaOH solution to pH 8. The mixture is left stirring for one hour and is then extracted three times with ethyl acetate. The organic phases are washed with water to neutral pH. The organic phase is dried over $MgSO_4$ and the solvent is evaporated off. The residue obtained is then purified by chromatography on a column of silica eluted with an acetone/toluene/cyclohexane mixture (5/3/2). The residue obtained is then recrystallized from cyclohexane, and then from an ether/petroleum ether mixture.

Characteristics:

MW: 231.28 g. $Mol^{-1}$ Appearance: white solid m.p.: 60°–61° C. Yield: 50%

Infrared Spectroscopic Analysis:

3290 $cm^{-1}$: vNH 2840–3000 $cm^{-1}$: vCH 1630 $cm^{-1}$: vC=O

Proton NMR Spectroscopic Analysis (300 MHz, $CDCl_3$):

$\delta$=1.28 ppm (triplet, 3H): $H_a$ $\delta$=1.96 ppm (singlet, 3H): $H_e$ $\delta$=2.75 ppm (quartet, 2H): $H_b$ $\delta$=2.90 ppm (triplet, 2H): $H_c$ $\delta$=3.60 ppm (quartet, 2H): $H_d$ $\delta$=5.55 ppm (signal, 1H): NH $\delta$=7.16 ppm (doubled doublet, 1H): $H_6$ $\delta$=7.44 ppm (multiplet, 2H): $H_7$+$H_4$ $\delta$=7.5 ppm (singlet, 2H): $H_2$

| | Microanalysis: | | |
|---|---|---|---|
| | % C | % H | % N |
| theory | 72.70 | 7.41 | 6.06 |
| found | 72.45 | 7.50 | 6.13 |

EXAMPLES 2 TO 12

Working as in Example 1, but using the appropriate acyl chloride or acid anhydride, the compound of the following examples is obtained:

Example 2: N-[2-(5-ethylbenzofuran-3-yl)ethyl]-2-chloroacetamide
Example 3: N-[2-(5-ethylbenzofuran-3-yl)ethyl] propionamide
Example 4: N-[2-(5-ethylbenzofuran-3-yl)ethyl]butyramide
Example 5: N-[2-(5-ethylbenzofuran-3-yl)ethyl] pentanamide
Example 6: N-[2-(5-ethylbenzofuran-3-yl)ethyl] hexanamide
Example 7: N-[2-(5-ethylbenzofuran-3-yl)ethyl] heptanamide
Example 8: N-[2-(5-ethylbenzofuran-3-yl)ethyl] cyclopropanecarboxamide
Example 9: N-[2-(5-ethylbenzofuran-3-yl)ethyl] cyclobutanecarboxamide
Example 10: N-[2-(5-ethylbenzofuran-3-yl)ethyl] cyclopentanecarboxamide
Example 11: N-[2-(5-ethylbenzofuran-3-yl)ethyl] cyclohexanecarboxamide
Example 12: N-[2-(5-ethylbenzofuran-3-yl)ethyl] trifluoroacetamide

EXAMPLES 13 TO 42

Working as in Example 1, but starting with preparations 2 to 6 and using the appropriate acyl chlorides and acid anhydrides, the compounds of the following examples are obtained.

Example 13: N-[2-(5-propylbenzofuran-3-yl)ethyl] acetamide
Example 14: N-[2-(5-propylbenzofuran-3-yl)ethyl] propionamide
Example 15: N-[2-(5-propylbenzofuran-3-yl)ethyl] butyramide
Example 16: N-[2-(5-propylbenzofuran-3-yl)ethyl] pentanamide
Example 17: N-[2-(5-propylbenzofuran-3-yl)ethyl] cyclopropanecarboxamide
Example 18: N-[2-(5-propylbenzofuran-3-yl)ethyl] cyclobutanecarboxamide
Example 19: N-[2-(5-butylbenzofuran-3-yl)ethyl]acetamide
Example 20: N-[2-(5-butylbenzofuran-3-yl)ethyl] propionamide
Example 21: N-[2-(5-butylbenzofuran-3-yl)ethyl] butyramide
Example 22: N-[2-(5-butylbenzofuran-3-yl)ethyl] pentanamide
Example 23: N-[2-(5-butylbenzofuran-3-yl)ethyl] cyclopropanecarboxamide
Example 24: N-[2-(5-butylbenzofuran-3-yl)ethyl] cyclobutanecarboxamide
Example 25: N-[2-(5-hexylbenzofuran-3-yl)ethyl]acetamide
Example 26: N-[2-(5-hexylbenzofuran-3-yl)ethyl] propionamide
Example 27: N-[2-(5-hexylbenzofuran-3-yl)ethyl] butyramide
Example 28: N-[2-(5-hexylbenzofuran-3-yl)ethyl] pentanamide
Example 29: N-[2-(5-hexylbenzofuran-3-yl)ethyl] cyclopropanecarboxamide
Example 30: N-[2-(5-hexylbenzofuran-3-yl)ethyl] cyclobutanecarboxamide
Example 31: N-[2-(5-cyclopropylbenzofuran-3-yl)ethyl] acetamide
Example 32: N-[2-(5-cyclopropylbenzofuran-3-yl)ethyl] propionamide
Example 33: N-[2-(5-cyclopropylbenzofuran-3-yl)ethyl] butyramide
Example 34: N-[2-(5-cyclopropylbenzofuran-3-yl)ethyl] pentanamide
Example 35: N-[2-(5-cyclopropylbenzofuran-3-yl)ethyl] cyclopropanecarboxamide
Example 36: N-[2-(5-cyclopropylbenzofuran-3-yl)ethyl] cyclobutanecarboxamide
Example 37: N-[2-(5-cyclopropylmethylbenzofuran-3-yl) ethyl]acetamide
Example 38: N-[2-(5-cyclopropylmethylbenzofuran-3-yl) ethyl]propionamide
Example 39: N-[2-(5-cyclopropylmethylbenzofuran-3-yl) ethyl]butyramide
Example 40: N-[2-(5-cyclopropylmethylbenzofuran-3-yl) ethyl]pentanamide
Example 41: N-[2-(5-cyclopropylmethylbenzofuran-3-yl) ethyl]cyclopropanecarboxamide
Example 42: N-[2-(5-cyclopropylmethylbenzofuran-3-yl) ethyl]cyclobutanecarboxamide

EXAMPLES 43 TO 47

The compounds of the following examples are obtained using the amine obtained by hydrogenation of preparation 1 and the appropriate isocyanate or isothiocyanate derivative.

Example 43: N-[2-(5-ethylbenzofuran-3-yl)ethyl]-N'-methylurea
Example 44: N-[2-(5-ethylbenzofuran-3-yl)ethyl]-N'-ethylurea
Example 45: N-[2-(5-ethylbenzofuran-3-yl)ethyl]-N'-propylurea
Example 46: N-[2-(5-ethylbenzofuran-3-yl)ethyl]-N'-cyclopropylurea
Example 47: N-[2-(5-ethylbenzofuran-3-yl)ethyl]-N'-cyclobutylurea

EXAMPLES 48 TO 52

The compounds of the following examples are obtained using the amine obtained by hydrogenation of preparation 2 and the appropriate isocyanate or isothiocyanate derivative.

Example 48: N-[2-(5-propylbenzofuran-3-yl)ethyl]-N'-methylurea

Example 49: N-[2-(5-propylbenzofuran-3-yl)ethyl]-N'-ethylurea

Example 50: N-[2-(5-propylbenzofuran-3-yl)ethyl]-N'-propylurea

Example 51: N-[2-(5-propylbenzofuran-3-yl)ethyl]-N'-cyclopropylurea

Example 52: N-[2-(5-propylbenzofuran-3-yl)ethyl]-N'-cyclobutylurea

EXAMPLES 53 TO 55

Working as in Example 1, but starting with preparations 7 to 9, the compounds of the following examples are obtained.

Example 53: N-[2-(5-ethyl-2,3-dihydrobenzofuran-3-yl)ethyl]acetamide

Example 54: N-[2-(5-propyl-2,3-dihydrobenzofuran-3-yl)ethyl]acetamide

Example 55: N-[2-(5-butyl-2,3-dihydrobenzofuran-3-yl)ethyl]acetamide

Example 56: N-[2-(6-ethyl-benzofuran-3-yl)ethyl]acetamide

PHARMACOLOGICAL STUDY

EXAMPLE A

Study of the Acute Toxicity

The acute toxicity was evaluated after oral administration to batches of 8 mice (26±2 grams). The animals were observed at regular intervals on the first day and daily for the two weeks following the treatment. The $LD_{50}$, leading to the death of 50% of the animals, was evaluated.

The $LD_{50}$ of the test products is greater than 1000 mg $kg^{-1}$ for the test compounds which indicates the low toxicity of the compounds of the invention.

EXAMPLE B

Study of the Binding to the Melatonin Receptors

B1) Study On Sheep Pars Tuberalis Cells

The studies of the binding of the compounds of the invention to the melatonin receptors were performed according to the standard techniques, on sheep pars tuberalis cells. The pars tuberalis of the adenohypophysis is indeed characterized in mammals, by a high density of melatonin receptors (Journal of Neuroendocrinology vol. (1), pp 1–4 (1989)).

Procedure

1) Sheep pars tuberalis membranes are prepared and used as target tissue in saturation experiments in order to determine the binding capacities and affinities for 2-[$^{125}$I]-iodomelatonin.

2) The sheep pars tuberalis membranes are used as target tissue, with various test compounds, in competitive binding experiments relative to 2-[$^{125}$I]-melatonin.

Each experiment is performed in triplicate and a range of different concentrations is tested for each compound.

The results make it possible to determine, after statistical treatment, the binding affinities of the test compound.

Results

It is seen that the compounds of the invention possess a powerful affinity for the melatonin receptors, this affinity being stronger than that for melatonin itself.

B2) Study On Chick (*Gallus Domesticus*) Brain Cell Membranes

The animals used are 12-day old chicks (*Gallus domesticus*). They are sacrificed between 13.00 h and 17.00 h on the day of their arrival. The brains are rapidly removed and frozen at −200° C. and then stored at −80° C. The membranes are prepared according to the method described by Yuan and Pang (Journal of Endocrinology 128, pages 475–482, 1991). 2-[$^{125}$I]-melatonin is incubated in the presence of the membranes in a solution buffered to pH 7.4 for 60 min at 25° C. After this period, the membrane suspension is filtered (Whatman GF/C). The radioactivity retained on the filter is determined using a Beckman® LS 6000 liquid scintillation counter.

The products used are:

2-[$^{125}$I]-melatonin melatonin common products original molecules

In primary screening, the molecules are tested at 2 concentrations ($10^{-7}$ and $10^{-5}$M). Each result is the average of n=3 independent measurements. The active molecules retained according to the results of the primary screening formed the subject of a quantitative determination of their efficacy ($IC_{50}$). They are used at 10 different concentrations.

Thus, the $IC_{50}$ values found for the preferred compounds of the invention, which correspond to the values of the affinity, show that the binding of the test compounds is very powerful.

EXAMPLE C

Four-Plate Test

The products of the invention are administered esophageally to batches of ten mice. One batch receives gum syrup. 30 minutes after administration of the products to be studied, the animals are placed in chambers the floor of which comprises four metal plates. Each time the animal passes from one plate to another, it receives a mild electric discharge (0.35 mA). The number of passages is recorded for one minute. After administration, the compounds of the invention significantly increase the number of passages, which shows the anxiolytic activity of the derivatives of the invention.

EXAMPLE D

Compounds of the Invention On the Circadian Rhythms of Rat Locomotor Activity The involvement of melatonin in driving, via the alternating day/night cycle, most of the physiological, biochemical and behavioral circadian rhythms has made it possible to establish a pharmacological model for the search for melatoninergic ligands.

The effects of the molecules are tested on a number of parameters and in particular on the circadian rhythms of locomotor activity, which represent a reliable marker of the activity of the endogenous circadian clock.

In this study, the effects of such molecules on a particular experimental model, namely a rat placed in temporal isolation (permanent darkness), is evaluated.

17

Experimental Procedure

On their arrival at the laboratory, one-month-old male Long Evans rats are subjected to a lighting cycle of 12 h of light per 24 h (12:12 LD).

After 2 to 3 weeks of adaptation, they are placed in cages equipped with a wheel connected to a recording system so as to detect the phases of locomotor activity and thus to monitor the nyctohemeral (LD) or circadian (DD) rhythms.

As soon as the rhythms recorded show evidence of being stably driven by the 12:12 LD lighting cycle, the rats are placed in permanent darkness (DD).

Two to three weeks later, when the free, non-driven pattern (rhythm reflecting that of the endogenous clock) is clearly established, the rats receive a daily administration of the test molecule.

The observations are made by virtue of the visualization of the rhythms of activity:
- rhythms of activity driven by the lighting rhythm,
- disappearance of the driving pattern for the rhythms in permanent darkness,
- rhythms driven by the daily administration of the molecule; transient or long-lasting effect.

A software program makes it possible:
- to measure the duration and intensity of the activity, the period of the rhythm in the animals under free, non-driven conditions and during the treatment,
- possibly to demonstrate, by spectral analysis, the existence of circadian and non-circadian components (for example ultradian components).

Results:

It is clearly seen that the compounds of the invention make it possible to have a powerful effect on the circadian rhythm via the melatoninergic system.

EXAMPLE E

Antiarrythmic Activity

Procedure (Ref: Lawson J. W. et al. J. Pharmacol. Expert. Therap. 160: 22–31, 1968)

The test substance is administered intraperitoneally to a group of 3 mice 30 min before exposure to anesthesia by chloroform. The animals are then observed for 15 min. The absence of recording of arrythmia and of cardiac frequencies above 200 beats/min (control: 400–480 beats/min) in at least two animals indicates a significant protection.

EXAMPLE F

Platelet Anti-Aggregating Activity

Procedure (Ref.: Bertele V. et al. Science. 220: 517–519, 1983 Ibid, Eur. J. Pharmacol. 85: 331–333, 1982)

The compounds of the invention (100 µg/ml) are tested for their capacity to inhibit irreversible platelet aggregation induced by sodium arachidonate (50 µg/ml) in platelet-enriched rabbit plasma.

An inhibition of more than 50% in the maximum aggregation indicates a significant activity for the compounds of the invention.

This in vitro test shows that the compounds of the invention are good candidates for the treatment of cardiovascular diseases, in particular thrombosis.

18

EXAMPLE G

Prolongation of the Bleeding Time

Procedure (Ref.: Djana E. et al. Thrombosis Research. 15: 191–197, 1979) Butler K. D. et al. Thromb. Haemostasis. 47: 46–49, 1982)

The test compounds are administered orally (100 mg/kg) to a group of 5 mice 1 h before the standardized sectioning of the end of each tail (0.5 mm).

The mice are immediately suspended vertically, the tails being immersed to a depth of 2 cm in a test tube containing isotonic saline solution at 37° C.

The time required for the bleeding to stop for a period of 15 seconds is then determined.

A prolongation of more than 50% in the bleeding time relative to a control group of animals is considered as being significant for the compounds of the invention.

This in vivo test confirms the advantage of the compounds of the invention for the treatment of cardiovascular pathologies, since the compounds of the invention prolong the bleeding time.

EXAMPLE H

Test of Hypobaric Hypoxia

Procedure (Ref.: Gotti B., and Depoortere H., Circ. Cerebrale, Congress on Cerebral Circulation, Toulouse, 105–107, 1979)

The test compounds are administered intraperitoneally (100 mg/kg) to a group of 3 mice 30 minutes before they are placed in a chamber at a hypobaric pressure of 20 cm Hg.

The prolongation of the survival time, relative to a group of animals treated with the vehicle, by more than 100% in the absence of a depressant effect on the central nervous system indicates a cerebroprotective activity of the compounds of the invention.

EXAMPLE I

Pharmaceutical Composition: Tablets 1000 tablets containing a 5 mg dose of N-[2-(5-ethylbenzofuran-3-yl)ethyl]acetamide N-[2-(5-Ethylbenzofuran-3-yl)ethyl]acetamide 5 g
Wheat starch 20 g
Corn starch 20 g
Lactose 30 g
Magnesium stearate 2 g
Silica 1 g
Hydroxypropyl cellulose 2 g

We claim:

1. A method-of-treating a mammal afflicted with a disorder of the melatoninergic system comprising the step of administering to the said mammal an amount of a compound selected from the group consisting of those of formula (I):

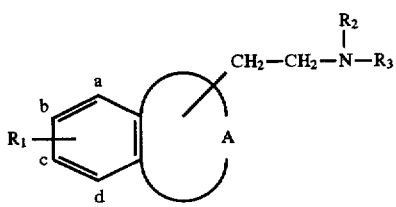

in which

R₁ represents alkyl,

A forms, with the benzene ring to which it is attached, a cyclic group selected from the group consisting of benzofuran and 2,3-dihydrobenzofuran, R₂ represents hydrogen, R₃ represents

with X representing oxygen and R₄ representing alkyl, it being understood that, in the description of formula (I), the term "alkyl" denotes a linear or branched group containing 1 to 6 carbon atoms, inclusive, and the enantiomers and diastereoisomers thereof, which is effective for alleviating the said disorder.

2. A method of claim 1, wherein, in the compound,

R₁ represents ethyl,

R₁ represents propyl, or

R₁ represents butyl, and

A forms, with the benzene ring to which it is attached, benzofuran.

3. A method of claim 1, wherein the compound corresponds to formula (1):

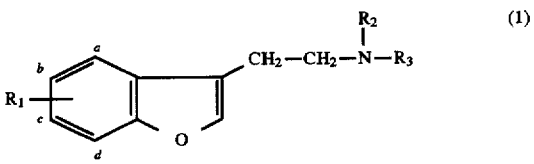

4. A method of claim 1, in which R₁ of the compound is in position b of the benzo ring.

5. A compound which is N-[2-(5-ethylbenzofuran-3-yl)ethyl]acetamide.

6. A pharmaceutical composition, useful in alleviating disorders of the melatoninergic system, containing a compound as claimed in claim 5, in combination with one or more pharmaceutically-acceptable excipients.

7. A method of treating a mammal afflicted with a disorder of the melatoninergic system comprising the step of administering to the said mammal an effective amount of a compound as claimed in claim 5 for alleviating the said disorder.

8. A method of treating sleeping disorders according to claim 7.

9. A method-of-treating sleeping disorders according to claim 1.

* * * * *

UNITED STATES PATENT AND TRADEMARK OFFICE
CERTIFICATE OF CORRECTION

PATENT NO. : 5,703,121
DATED     : Dec. 30, 1997
INVENTOR(S) : D. Lesieur, et al It is certified that error appears in the above-identified patent and that said Letters Patent is hereby corrected as shown below:

```
Column 3, line 50(approx.):  In the formula, "a,b,c,d"
     should be deleted.  Page 5, line 6
```

Signed and Sealed this

Sixteenth Day of June, 1998

Attest:

BRUCE LEHMAN

Attesting Officer

Commissioner of Patents and Trademarks